United States Patent [19]

Antognazza et al.

[11] Patent Number: 6,077,958

[45] Date of Patent: Jun. 20, 2000

[54] HETEROAROMATIC DIPHOSPHINES AS CHIRAL LIGANDS

[75] Inventors: Patrizia Antognazza, Locate Varesino; Tiziana Benincori, Milan; Elisabetta Brenna, Paina Di Giussano; Edoardo Cesarotti, Milan; Francesco Sannicolo', Milan; Licia Trimarco, Milan, all of Italy

[73] Assignee: Italfarmaco Sud S.p.A., Patrica FR, Italy

[21] Appl. No.: 09/300,531

[22] Filed: Apr. 27, 1999

Related U.S. Application Data

[62] Division of application No. 08/765,479, filed as application No. PCT/EP95/02647, Jul. 7, 1995, Pat. No. 5,907,045.

[30] Foreign Application Priority Data

Jul. 12, 1994 [IT] Italy .................................. MI94A1438

[51] Int. Cl.[7] ........................ C07F 9/6539; C07F 9/6553; B01J 31/24

[52] U.S. Cl. .......................... 548/101; 548/111; 548/119; 549/3; 549/6; 549/7; 502/162; 502/165; 502/166; 502/223; 502/221

[58] Field of Search .................... 502/162, 165, 502/221, 166, 223; 549/3, 6, 7; 556/13, 19, 20; 548/111, 119, 101

[56] References Cited

U.S. PATENT DOCUMENTS

| | | | |
|---|---|---|---|
| 3,966,595 | 6/1976 | Gosser | 549/6 |
| 4,755,611 | 7/1988 | Hill | 549/6 |
| 5,508,438 | 4/1996 | Broger | 549/6 |

FOREIGN PATENT DOCUMENTS

| | | |
|---|---|---|
| 151282 | 8/1985 | European Pat. Off. . |
| 643065 | 3/1995 | European Pat. Off. . |
| WO A92/16536 | 10/1992 | WIPO . |

OTHER PUBLICATIONS

Benincori J. Chem Soc., Chem Comm, Diphenylphosphino–biheteroaryls issue 6, pp. 686–686, Mar. 1994.

Benincori J. Org Chem "New Class of Chiral Diphosphine Ligands for Highly Efficient Transition Metal–catalyzed Stereoselective Reactions", 61 pp. 6244–6251, 1996.

Chemical Abstracts, vol. 089, No. 5, Jul. 31, 1978, Columbus, Ohio.

*Primary Examiner*—Johann Richter
*Assistant Examiner*—Jean F. Vollano
*Attorney, Agent, or Firm*—Collard & Roe, P.C.

[57] ABSTRACT

Chiral diphosphines are constituted by an aromatic pentatomic biheterocyclic system, suitable to act as chiral ligands and complexes between the diphosphines and transition metals. They may be utilized as chiral catalysts in stereocontrolled reactions, such as diastereo- and enantioselective reduction reactions. Process is for the preparation of these chiral diphosphines; and process is for the preparation of these complexes and for their utilization as chiral catalysts in stereocontrolled reactions.

4 Claims, No Drawings

HETEROAROMATIC DIPHOSPHINES AS CHIRAL LIGANDS

CROSS-REFERENCE TO RELATED APPLICATION

This patent application is a divisional patent application of U.S. patent application Ser. No. 08/765,479 filed Dec. 23, 1996, now U.S. Pat. No. 5,907,045 which is a 371 of PCT/EP95/02647 filed Jul. 7, 1995, which designated the United States.

Object of the present invention are chiral diphosphines, complexes between said diphosphines and transition metals, and their utilization as chiral catalysts in stereoselective (stereocontrolled) reactions, such as, for instance, diastereo- and enantioselective reduction reactions in general, or asymmetric isomerization in general.

Another object of the present invention is a process for the preparation of said chiral diphosphines, as well as a process for the preparation of said chiral complexes and their utilization as catalysts in diastereo- and enantioselective reactions.

Further another object of the present invention are stereoselective processes, in particular diastereo- and enantioselective reductions in general, which utilize said chiral catalysts.

PRIOR ART

As is known, stereoselective reactions, in particular the reactions of stereocontrolled reduction, such as, for instance, diastereo- and enatioselective hydrogenations, are of great importance and have been studied for a long time; in fact, such reactions lead directly to the formation of optically active compounds which would be obtainable otherwise only as racemates, with the ensuing need of a subsequent separation of the enantiomers and the related drawbacks which sometimes are found in performing such separation, with the associated high probability of failing to obtain the pure enantiomeric forms; besides, in these cases a further drawback may arise from the presence of an unwished enantiomer, which must be reconverted or disposed of.

In general, the stereocontrolled reduction reactions realized by means of chiral calalysts allow to obtain the optically active reaction products, often also with good enantiomeric excesses.

For instance, the first enantioselective hydrogenation reaction of unsaturated compounds was carried out through the utilization of metal catalysts deposited on chiral supports and goes back to the thirties. Afterwards, homogeneous asymmetric hydrogenation reactions have been studied and described that had been realized by means of special chiral catalysts, constituted by complexes between transition metals and chiral phosphines which acts as ligands towards the metal.

The literature reports on different types of chiral phosphines which can act as ligands and form chiral complexes with transition metals, such as, for instance, Ruthenium (Ru), Rhodium (Rh), Palladium (Pd), Iridium (Ir) and Platinum (Pt). In particular, chiral phosphines are characterized by one or two stereogenic atoms of phosphorus, which will have, in this case, three different substituents, such as, for instance, DIPAMP which (R,R) enantiomer has the following formula:

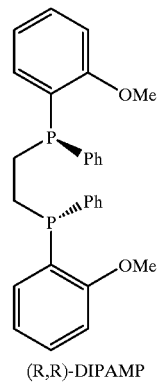

(R,R)-DIPAMP

[KNOWLES W. S. et. al., J. Chem. Soc. Chem. Commun. 10 (1972); VINEYARD B. D. et al., J. Am. Chem. Soc. 99, 5946(1977)]; phosphines are also described whose chirality is due to the presence of carbon-based stereocentres, such as for instance the compound known as CHIRAPHOS, which (S, S) enantiomer has the following formula:

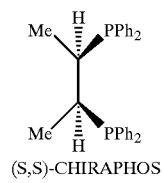

(S,S)-CHIRAPHOS

[FRYZUK M. D. et al. J. Am. Chem. Soc. 99, 6262(1977)]; also phosphines are reported whose chirality is due to the presence of an atropisomeric biaryl system, i.e. a system in which the rotation around the simple bond connecting two aryl groups is prevented. For example, WO 92/16536 discloses new racemic and optically active diphosphines, or chiral diphosphines, having a biphenyl structure. Said chiral phosphines are described as ligands in the preparation of complexes with group VIII metals, which complexes are useful as catalysts for asymmetrical hydrogenations and for enantioselective hydrogen shifts in prochiral allylic systems. The chirality of the described phosphines is due to the presence of the biphenyl structure which also renders the corresponding complexes suitable for being used as chiral catalysts.

EP 643065 also discloses a new diphosphine useful as catalyst for asymmetrical hydrogenations; the disclosed diphosphine is characterized by the presence of a biphenyl structure which is responsable for the chirality of the system.

Other diphosphines of this type are for instance BINAP, BIPHEMP or BICHEP, which (R) enantiomers have the following formulae:

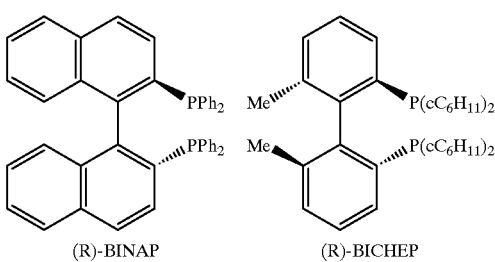

(R)-BINAP      (R)-BICHEP

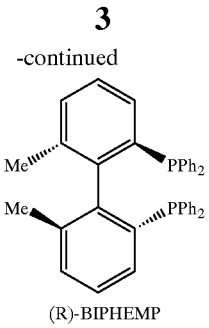

(R)-BIPHEMP

[NOYORI R. et al., J. Am. Chem. Soc. 102, 7932(1980); SCHMID R. et al. Helv. Chim. Acta 71, 897(1988); MIYASHITA A. et al., Chem. Lett. 1849(1989)].

At present, for instance, the catalysts for the stereocontrolled reduction, such as the diastereo- and enantioselective hydrogenation of carbonyl groups, which allow to obtain the best diastereomeric and enantiomeric excesses of secondary chiral alcohols, are those constituted by complexes between transition metals and chiral diphosphines by atropisomery, and in particular complexes between Ru and BINAP.

Of course, the main problem is that of the synthesis of the chiral diphosphine which acts as ligand. In the aforementioned cases, the process of synthesis of the chiral diphosphine is rather complicated, as it involves numerous steps; besides, the diphosphine which is obtained as a racemate needs a laborious resolution process, with low yields and very high costs. As a consequence, the chiral catalyst obtained by formation of a complex between the chiral diphosphine and a transition metal may be very expensive.

AIMS OF THE INVENTION

An aim of the present invention is to provide a chiral diphosphine suitable for acting as a ligand for transition metals through the formation of particularly stable coordination bonds.

Another aim of the invention is to provide a chiral diphosphine such as to be obtainable more easily from the synthetic point of view compared to the known art. Still another aim of the invention is to provide a process for the preparation of a chiral diphosphine suitable to act as a ligand for transition metals, consisting of simple steps, having contained costs and being industrially applicable.

Still a further aim of the present invention is to provide a new chiral catalyst to be used in stereocontrolled synthesis reactions.

Another aim of the invention is to provide a chiral catalyst to be used in stereocontrolled synthesis reactions, such as to be highly reactive and provided with a high regio-, chemo-, diastereo-, enantio-selectivity.

Still a further aim of the present invention is to provide a chiral catalyst to be used in stereocontrolled synthesis reactions, such as to allow to operate in mild reaction conditions, obtaining anyway high reaction rates.

Another aim of the invention is to allow the realization of stereocontrolled reactions, in particular reduction reactions or isomerization reactions involving the utilization of a chiral catalyst and leading to the formation of optically active products with high diastereomeric or enantiomeric excesses.

DESCRIPTION OF THE INVENTION

These and still other aims and associated advantages which will be more clearly expounded in the following description, are reached by a chiral diphosphine constituted by an aromatic pentatomic biheterocyclic system.

More particularly, said chiral diphosphine constituted by an aromatic pentatomic biheterocyclic system has the following general formula:

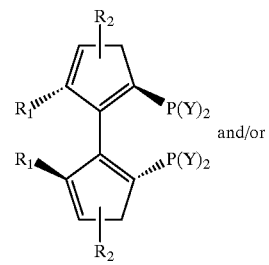

(IA)

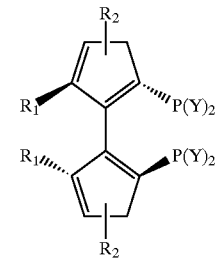

(IB)

where:

$R_2$ is chosen among hydrogen, phenyl, aryl, linear, branched, cyclic alkyl $C_1$–$C_{10}$, $COOR_3$, where $R_3$ is linear, branched, cyclic alkyl $C_1$–$C_{10}$;

Y is chosen among phenyl, substituted phenyl, aryl, substituted aryl, linear, branched, cyclic alkyl $C_3$–$C_{10}$;

$R_1$ is chosen among phenyl, substituted phenyl, aryl, substituted aryl, linear, branched, cyclic alkyl $C_1$–$C_{10}$, $OR_5$, where $R_5$ is linear, branched, cyclic alkyl $C_1$–$C_{10}$, or each pentatomic heterocyclic aromatic ring of said system is condensated to a substituted or unsubstituted benzene or naphthalene ring, according to the following formula:

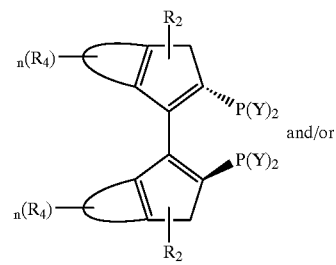

(IIA)

-continued (IIB)

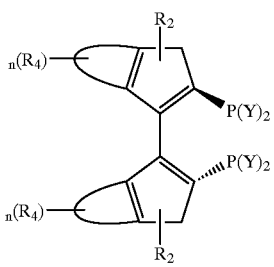

where n ranges from 0 to 6, $R_2$ may also be equal to zero, $R_4$ is chosen among hydrogen, linear, branched, cyclic, substituted or unsubstituted alkyl $C_1–C_{10}$.

The aforementioned graphic representation is to be construed as being non limitative, meaning that, for instance, each of said pentatomic heterocyclic aromatic rings is condensed to said substituted or unsubstituted benzene or naphthalene ring also according to the following formula:

(VA)

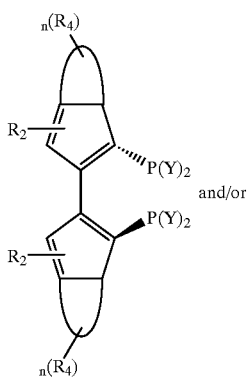

and/or (VB)

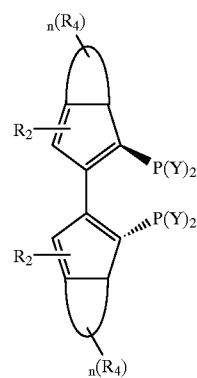

where $R_4$, n, $R_2$ are defined as above.

The aromatic pentatomic biheterocyclic system is chosen among:
1,1'-bipyrrole, 2,2'-bipyrole, 3,3'-bipyrrole
3,3'-bithiophenee
3,3'-bifuran
1,1'-biimidazole
and the corresponding benzocondensed (II A) (II B), (V A) (V B), 4,4'-bipyrazole, 5,5'-bipyrazole
1,1'-bi-1,3,4-triazole
4,4'-biisoxazole
4,4'-biisothiazole
5,5'-biimidazole
3,3-bibenzothiophenes
3,3'-bibenzofurans,
2,2'-biindoles
1,1'-bibenzoimidazoles.

The chiral diphosphines having the following formulae:

(IIIR)

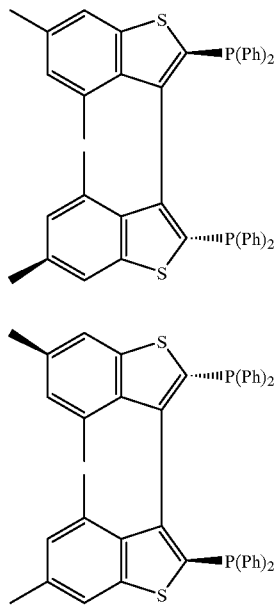

(IIIS)

(IVR)

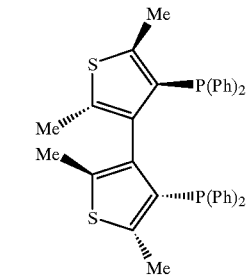

(IVS)

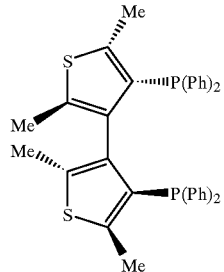

proved to be particularly advantageous according to the present invention.

Also the chiral diphosphine having the following formula:

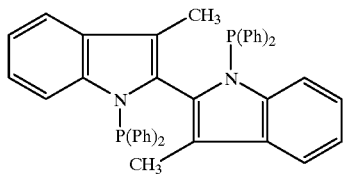
(VIR) or (VIS)

proved to be particularly advantageous, always according to the present invention.

Also the chiral diphosphines having the following formula:

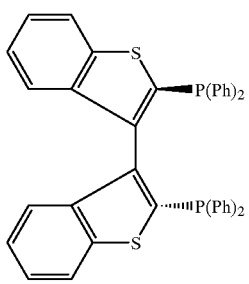
(VIIR)

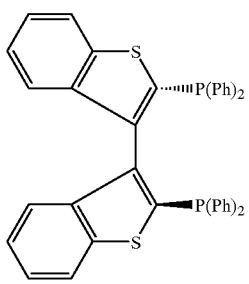
(VIIS)

proved to be particularly advantageous, always according to the invention.

In another embodiment, the present invention provides a chiral catalyst for stereocontrolled synthesis comprising a complex between a transition metal and a chiral diphosphine constituted by an aromatic pentatomic biheterocyclic system where said chiral diphosphine is constituted by an aromatic pentatomic biheterocyclic system having the following formula:

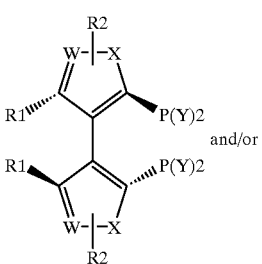
(IA)
and/or

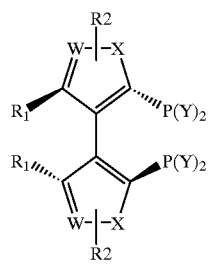
(IB)

where X is C or S; W is C or S; and with the proviso that only one of X or W is S;

where $R_2$ is selected from the group consisting of hydrogen, phenyl, aryl, linear, branched, or cyclic alkyl $C_1$–$C_{10}$, $COOR_3$, where $R_3$ is linear, branched, or cyclic alkyl $C_1$–$C_{10}$;

Y is selected from the group consisting of phenyl, substituted phenyl where substituents are selected from the group consisting of linear, branched, or cyclic alkyl $C_1$–$C_{10}$, halogen, $OR_6$ where $R_6$ is linear, branched, or cyclic alkyl $C_1$–$C_{10}$, aryl, substituted aryl where substituents are selected from the group consisting of linear, branched, or cyclic alkyl $C_1$–$C_{10}$, halogen, $OR_6$ where $R_6$ is linear, branched, or cyclic alkyl $C_1$–$C_{10}$, linear, branched, or cyclic alkyl $C_3$–$C_{10}$;

$R_1$ is selected from the group consisting of phenyl, substituted phenyl where substituents are selected from the group consisting of linear, branched, or cyclic alkyl $C_1$–$C_{10}$, halogen, $OR_6$ where $R_6$ is linear, branched, or cyclic alkyl $C_1$–$C_{10}$, aryl, substituted aryl where substituents are selected from the group consisting of linear, branched, or cyclic alkyl $C_1$–$C_{10}$, halogen, $OR_6$ where $R_6$ is linear, branched, or cyclic alkyl $C_1$–$C_{10}$, linear, branched, or cyclic alkyl $C_1$–$C_{10}$, $OR_5$, where $R_5$ is linear, branched, or cyclic alkyl $C_1$–$C_{10}$, or each pentatomic heterocyclic aromatic ring of said system is optionally fused to an optionally substituted benzene or naphthalene ring, wherein the optional substituents are selected from among the group consisting of linear, branched, or cyclic alkyl $C_1$–$C_{10}$, halogen, $OR_6$ where $R_6$ is linear, branched, or cyclic alkyl $C_1$–$C_{10}$, or unsubstituted according to the following formula:

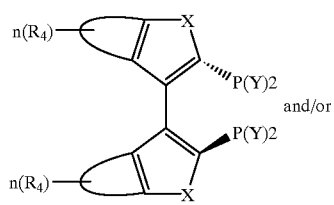
(IIA)
and/or

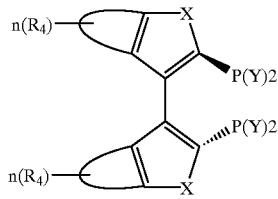
(IIB)

where X is S;

or according to the following formula:

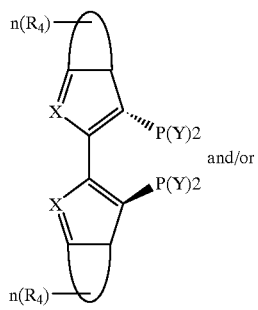
(VA)

and/or

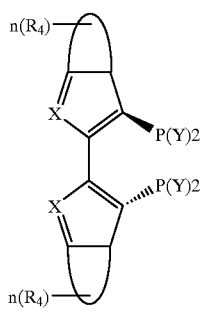
(VB)

where X is S; and where $R_4$ is selected from the group consisting of hydrogen, linear, branched, cyclic, or unsubstituted alkyl $C_1$–$C_{10}$, n ranges from 0 to 6;

or the aromatic pentatomic biheterocyclic system is selected from the group consisting of:

3,3'-bithiophene, and the corresponding benzocondensates (II A) (II B), (V A) (V B), and 3,3'-bibenzothiophenes.

In a further embodiment, the present invention provides a chiral catalyst for stereocontrolled synthesis comprising a complex between a transition metal and a chiral diphosphine constituted by an aromatic pentatomic biheterocyclic system where said chiral diphosphine is constituted by an aromatic pentatomic biheterocyclic system having the following formula:

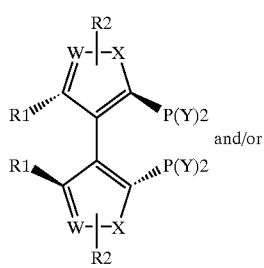
(IA)

and/or

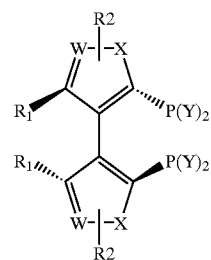
(IB)

where X is N or S; W is N or S; and with the proviso that only one of X or W is S;

where $R_2$ is selected from the group consisting of hydrogen, phenyl, aryl, linear, branched, or cyclic alkyl $C_1$–$C_{10}$, $COOR_3$, where $R_3$ is linear, branched, or cyclic alkyl $C_1$–$C_{10}$;

Y is selected from the group consisting of phenyl, substituted phenyl where substituents are selected from the group consisting of linear, branched, or cyclic alkyl $C_1$–$C_{10}$, halogen, $OR_6$ where $R_6$ is linear, branched, or cyclic alkyl $C_1$–$C_{10}$, aryl, substituted aryl where substituents are selected from the group consisting of linear, branched, or cyclic alkyl $C_1$–$C_{10}$, halogen, $OR_6$ where $R_6$ is linear, branched, or cyclic alkyl $C_1$–$C_{10}$, linear, branched, or cyclic alkyl $C_3$–$C_{10}$;

$R_1$ is selected from the group consisting of penyl, substituted phenyl where substituents are selected fom the group consisting of linear, branched, or cyclic alkyl $C_1$–$C_{10}$, halogen, $OR_6$ where $R_6$ is linear, branched, or cyclic alkyl $C_1$–$C_{10}$, aryl, substituted aryl where substituents are selected from the group consisting of linear, branched, or cyclic alkyl $C_1$–$C_{10}$, halogen, $OR_6$ where $R_6$ is linear, branched, or cyclic alkyl $C_1$–$C_{10}$, linear, branched, or cyclic alkyl $C_1$–$C_{10}$, $OR_5$, where $R_5$ is linear, branched, or cyclic alkyl $C_1$–$C_{10}$, or 4,4'-biisothiazole, or 3,3'-bibenzothiophenes.

In particular, the chirality of said diphosphines (I A) (I B), (II A) (II B), (V A) (V B) is due to the presence of the pentatomic aromatic biheterocyclic system, which is a $C_2$ symmetry atropisomeric system, i.e. characterized by a high rotatory barrier around the bond connecting the two heterocyclic systems ([Eliel; Stereochemistry of Carbon Compounds, Int.Stud.Edition McGraw Hill—Tokyo 1962—p. 156 foll.].

Besides, said diphosphines according to the present invention are characterized in that the heterocyclic system, when it is electron-rich, increases the electronic availability of the phosphorus atom. Thanks to these characteristics, the diphosphines according to this invention are advantageously utilized as chiral ligands in the preparation of complexes with transition metals in which the coordination bond with the metal is helped precisely thanks to the electronic availability of the ligand, lended to the phosphorus atom by the heterocyclic system; such complexes are in their turn utilized as chiral catalysts in stereocontrolled syntheses, in particular in the diastereo- and enantioselective reduction reactions, such as for instance the hydrogenation reactions.

Always according to the present invention, said chiral diphosphines are prepared according to a process consisting of simple steps.

Always according to the invention and solely by way of example, a general process for the preparation of a chiral diphosphine having the general formula (I A) (I B) is schematically expounded. Said process comprises the following steps:

synthesis of the pentatomic aromatic biheterocyclic system through oxidative coupling of the corresponding pentatomic heterocyclic anion;

formation of the di-anion of the biheterocyclic system;

reaction of said di-anion with P(Y)$_2$Cl or PO(Y)$_2$Cl, where Y is chosen among phenyl, substituted phenyl, aryl, substituted aryl, linear, branched, cyclic alkyl C$_3$–C$_{10}$, obtaining the racemic diphosphine (I A)+(I B) or the racemic diphosphionoxide;

conversion of said racemic diphosphine (I A)+(I B) into the corresponding racemic diphosphinoxide by oxidation reaction according to known techniques;

reaction of said racemic diphosphinoxide with an acid chiral resolving agent, obtaining two diastereoisomeric adducts;

separation of said diastereomeric adducts by fractional crystallization;

basic treatment of each of said two separated diastereomeric adducts, to give the corresponding enantiomerically pure diphosphinoxides;

reduction of said enantiomerically pure diphosphinoxides with known reducing agents, such as, for instance, silanes, to give said enantiomerically pure chiral diphosphines (I A) and (I B).

Obviously, the aromatic biheterocyclic system may be prepared also according to other techniques known to the technicians of this sector. Besides, said formation of the di-anion of the biheterocyclic system may happen, in case of nitrogenated heterocyclic rings, also on the nitrogen atom.

More particularly, always according to this invention, said racemic diphosphine (I A)+(I B) may be advantageously directly resolved by column chromatography with the use of chiral means, such as the stationary phase, the eluent system and the like.

Still, said acid chiral resolving agent is preferably chosen, for instance, among dibenzoyltartaric acid, ditoluyltartaric acid, camphorsulphonic acids and the like.

As said already, the chiral diphosphines according to the present invention are utilized as ligands for the complexation of transition metals, in particular the metals of the VIII group, such as for instance Ru, Rh, Pd, Pt, Ir, to form chiral complexes which act as catalysts in stereocontrolled reactions.

According to the invention, said complexes between the chiral ligand and the metal are preferably obtained by an exchange reaction between the chiral diphosphine and a complex of the chosen metal, in which the bond between metal and ligand must be more labile than the bond that will form between metal and diphosphine; in this way, the diphosphine will substitute for the ligand in the coordination to the metal, forming a preferred coordination bond. In particular, in the above exchange reaction, the metal is utilized in coordination with ligands such as for instance 1,5-cis,cis-cyclooctadiene, norbornadiene, (ethylene)$_2$, triarylstibine, benzonitrile and the like.

In particular, the complex constituted by the chosen metal and the ligand is dissolved in a suitable solvent and then the chiral diphosphine is added, either in the solid state or dissolved in its turn in a suitable solvent; the progress of the reaction and hence the formation of the chiral complex, is followed through the examination of possible colour changes, as well as by means of spectroscopic methods, for instance by $^{31}$P-NMR, and GC. At the end of the reaction, the solvent is eliminated and the chiral complex formed may be utilized as it is or it may be subjected to a further purification according to known techniques.

The solvents preferably utilized for the preparation of the chiral complex are, for instance, chlorinated solvents, alcohols, aromatic hydrocarbons (toluene), ethers, dimethylformamide. The above chiral complexes are preferably prepared at the time when they are used as catalysts in stereocontrolled reactions.

Always according to the present invention, the chiral catalysts constituted by complexes between the chiral diphosphine and transition metals turn out to be more selective compared to those utilized in the known art; in fact, the geometry of the diphosphine ligand according to this invention may determine different bonds lengths and bond angles compared to those of the known traditional ligands, and consequently the stereoelective reactions which utilize said chiral catalysts provide advantages such as a remarkable reaction rate, mild reaction conditions, for instance as it concerns pressure and temperature conditions and the quantity of catalyst utilized, as well as the possibility of using solvents having a lower ecological impact.

Besides, said chiral catalysts have a high chemo-, enantio- and diastereo-selectivity and are advantageously utilized to perform stereocontrolled reactions, in particular diastereo- and enantioselective reduction reactions, such as, for instance, reduction of olefins (—C=C—), reduction of ketone carbonyl groups (—C=O), reduction of imine groups (—C=N—), reduction of enamines (—N—C=C—), obtaining optically active compounds with high diastereomeric and enantiomeric excesses.

Always according to the present invention, said chiral catalysts are utilized to carry out hydroformylation reactions, hydrocyanation reactions and double bond isomerization reactions. By way of non limitative example of this invention, the preparation of some chiral diphosphines (III R), (III S), (IV R) (IV S), (VI R) (VI S), (VII R) (VII S), (VIII R) (VIII S), the preparation of some chiral complexes between said diphosphines and the metals Ru and Rh respectively, as well as the utilization of said complexes as chiral catalysts according to this invention are described as follows; for instance, their utilization in the reduction of ethyl 3-oxo-butyrate, methyl 2-oxocyclopentanecarboxylate, α-acetamidocinammic acid and other ones.

EXAMPLE 1

Preparation of the chiral diphosphines (III R) and (III S)

a) Synthesis of 4,4',6,6'-tetramethyl-3,3'-dibenzo[b]thiophene 4.1 g of 3-bromo-4,6-dimethyl-benzo[b]thiophene dissolved in 11 ml of anhydrous ether were dripped under stirring in a solution of BuLi 1.6M (12 ml) in 11 ml of anhydrous ether, cooled to –70° C. The reaction mix was let to rest for 30 min, then 2.7 g of CuCl$_2$ were added and the reaction mix was kept under stirring for 6 hours, then was cooled at 0° C., then 17 ml of HCl 2M were added, and left to rest overnight. Then the organic salts that had formed were eliminated, and the organic phase was extracted with ether, made anhydrous on Na$_2$SO$_4$, and the solvent was eliminated under reduced pressure. The residue obtained was subject to silica gel column chromatography, utilizing hexane as eluent, the intermediate fractions were collected, freed from the solvent under reduced pressure, obtaining in this way 0.70 g of 4,4',6,6'tetramethyl-3,3'-dibenzene[b]thiophene.?

$^1$H-NMR (300 MHz) (CDCl$_3$) (ppm): 1.9 (6H, s, 2CH$_3$), 2.4 (6H, s, 2CH$_3$), 6.9 (2H, s, aromatic in 5,5'), 7.2 (2H, s, thiophenic), 7.5 (2H, s aromatic in the positions 7,7').

Mass spectrometry (e.i.): (M$^+$) 322.

b) Synthesis of 2,2'-bis(diphenylphosphin)-4,4',6,6'-tetramethyl-3,3'-dibenzo[b]thiophene.

In a solution of 0.35 g of 4,4',6,6'-tetramethyl-3,3'-dibenzo[b]thiophene and 0.39 g of TMEDA in 20 ml of anhydrous THF, 1.1 ml of BuLi of 1.6M were dripped in inert atmosphere and at a temperature of −50° C. After half an hour, the temperature was raised to 0° C. and 0.5 ml of diphenylchlorophosphine were dripped. The reaction mix was left to react for 12 hours and then was freed from the solvent under reduced pressure and treated with water. The organic phase was extracted with ether, made anhydrous on $Na_2SO_4$, and the solvent was eliminated under reduced pressure. The residue obtained was treated with isopropylether and 0.4 g of 2,2'-bis (diphenylphosphin)-4,4',6,6'-tetramethyl-3,3'-dibenzo[b]thiophene were obtained.

$^1$H-NMR (300 MHz) (CDCl$_3$) (ppm): 1.6 (6H, s, 2CH$_3$), 2.4 (6H, s, 2CH$_3$), 6.7 (2H, s, aromatic in 5,5'), 6,9–7,5 (22H, m, aromatic in 7,7'+4C$_6$H$_5$).

Mass spectrometry (e.g.): (M$^+$) 690.

$^{31}$P-NMR (200 MHz) (CDCl$_3$) (ppm): −24.98 (2P, s).

c) Oxidation of the racemic diphosphine to diphosphinoxide.

2 ml of $H_2O_2$ were added by dripping to a solution of 1.4 g of diphosphine obtained according to b) in 80 ml of $CH_2Cl_2$ at 0° C. The temperature was kept at 0° C. for 1 h and at 25° C. for 1 h, then 10 ml of water were added and the organic phase was separated, made anhydrous and freed from the solvent under reduced pressure.

1.5 g of the reaction mix were chromatographied, utilizing an AcOEt/CH$_2$Cl$_2$/Et$_3$N 3/7/0,1 eluent mix (v/v). The tail fractions were collected and 1.4 g of racemic diphosphinoxide were obtained, with a 96% yield.

$^1$H-NMR (300 MHz) (CDCl$_3$) (ppm): 1.5 (6H, s, 2CH$_2$), 2.4 (6H, s, 2CH$_3$), 6.7 (2H, s, aromatic in 5,5'), 7.0–7.8 (22H, m, aromatic in 7,7$^4$+4C$_6$H$_5$).

Mass spectrometry (e.i.): (M$^+$) 772.

$^{31}$P-NMR (200 MHz) (CDCL$_3$) (ppm): 20.36 (2 P=O, s).

d) Resolution: diphosphinoxide (-).

1.2 g of a mix of racemic diphosphinoxide obtained as in c) and 0.63 g of (−)-O,O'-dibenzoyl-L-tartaric acid (DBTA) were hot dissolved in 58 ml of a mix constituted by AcOEt/CHCl$_3$ 50:8 (v/v). After 24 h, 500 mg of an adduct were obtained by filtration between the diphosphinoxide (−) and the DETA (−), with melting point=218–220° C. and $[\alpha]_D^{25}$=−143° C. (c=0.55 in EtOH).

e) Treatment of the adduct of point d).

500 mg of adduct were treated with 9.6 ml of NaOH 0.75 N and the mix was extracted twice with 2 portions of 9.6 ml of CHCl$_3$. The organic phases so obtained were combined, washed with 6,4 ml of NaOH 0.75N, 6.4 ml of water and dried on $Na_2SO_4$.

The mix was filtered, the solvent evaporated under reduced pressure and 320 mg of chiral diphosphinoxide (−) were obtained. The so obtained diphosphinoxide has a value of $[\alpha]_D^{25}$=−226° (c=0.45, solvent benzene).

f) Resolution: diphosphinoxide (+).

The filtrate resulting from the process of point d) was freed from the solvent under reduced pressure, obtaining a residue of 1 g which was treated with 18 ml of NaOH 0.75N and extracted twice with 18 ml of CHCl$_3$.

The collected organic phases were washed with 12 ml of NaOH 0.75N and 12 ml of water, then were made anhydrous on $Na_2SO_4$ and the solvent was eliminated under reduced pressure. 0.60 g of diphosphinoxide (+) impure of diphosphinoxide (−) were obtained. The so obtained mix was combined to 0.312 g of DETA (+) and the whole was hot dissolved with 29 ml of a solution constituted by AcOEt/CHCl$_3$ 25/4 (v/v). After 24 h, the mix was filtered and 0.4 g of a solid constituted by an adduct between the diphosphinoxide (+) and the DBTA (+) were obtained, with a melting point=216–220° C. and an $[\alpha]_D^{25}$=+147 (c=0.55, EtOH).

The adduct was treated as described under e) and diphosphinoxide (+) was obtained, characterized by a value of $[\alpha]_D^{25}$=+229° (c=0.56, benzene).

g) Reduction.

0.4 g of diphosphinoxide (+) obtained as described under f) were dissolved in 6 ml of xylene and 0.59 ml of Et$_3$N and 0.42 of HSiCl$_3$ were added in inert conditions. The reaction mix was heated for 1 h at 100° C., for 1 h at 120° C. and for 6 h at 140° C. The remaining xylene and trichlorosilane were then eliminated under reduced pressure, the residue was treated with water and extracted with 20 ml of $CH_2Cl_2$. The reaction mix was then made anhydrous, the solvent eliminated under reduced pressure and the crude so obtained was chromatografied with flash chromatography in inert atmosphere, utilizing as eluent an hexane/CH$_2$Cl$_2$ 7/3 mix (v/v). 350 mg of diphosphine (+) were obtained, characterized by a value of $[\alpha]_D^{25}$=+215° (c=0.4, benzene). The diphosphinoxide (−), obtained as described under e) was reduced to diphosphine (−) by an analogous process and analogous yields were obtained; the diphosphine (−) is characterized by a value of $[\alpha]_D^{25}$=−222 (c=0.4, benzene).

EXAMPLE 2

Preparation of the chiral diphosphines (IV R) and (IV S).

a) Preparation of 2,2',5,5'-tetramethyl-3,3'-dithiophene.

5.46 g of 3-bromo-2,5-dimethylthiophene dissolved in 5 ml of ethyl ether were dripped in 18 ml of a BuLi solution 1.5M kept in nitrogen atmosphere at a temperature of −70° C. After 30 minutes, 4.13 g of anhydrous cupric chloride were added under strong stirring and the reaction mix was kept under stirring for 3 hours. The temperature was raised to 0° C. and then a HCl 6N solution was added to solubilize cupric chlorides. The aqueous phase was extracted with 120 ml of ether and the ether phase was treated with 15 ml of water, then with 12 ml of a saturated solution of sodium carbonate and again with 12 ml of water. The solution was then made anhydrous on sodium sulfate and the solvent was eliminated under reduced pressure; the so obtained residue was chromatographied on silica gel, eluting with hexane. The intermediate fractions were collected and 1.73 g of 2,2',5,5'-tetramethyl-3,3'-dithiophene were obtained, with a 55% yield.

$^1$H-NMR (300 MHz) CDCL$_3$) (ppm): 6.52 (2H, broad s, aromatic H in 4,4'), 2.41 (6H, s, 2CH$_3$), 2.27 (6H, s, 2CH$_3$).

b) Preparation of 4,4'-dibromo-2,2',5,5'-tetramethyl- 3,3'-dithiophene.

0.5 ml of bromine dissolved in carbon tetrachloride were dripped in a solution constituted by 1.97 g of 2,2',5,5'-tetramethyl-3,3'-dithiophene in 12 ml of carbon tetrachloride at 0° C.; the temperature was raised and after 15 minutes, keeping the temperature at 40° C., the same quantity of bromine dissolved in the same volume of carbon tetrachloride was dripped. After 30 minutes, 100 ml of methylenchloride were added, the mix was washed with 20 ml of a saturated solution of sodium carbonate, with 20 ml of water, and then the organic phase was made anhydrous on sodium sulfate. The solvent was eliminated under reduced pressure and 3.60 g of an oily residue were obtained, and said residue was chromatographied on silica gel, eluting in hexane. The head fractions were collected, the solvent was evaporated under reduced pressure and 1.47 g of 4,4'-dibromo-2,2',5,5'-tetramethyl-3,3'-dithiophene were obtained, with a 44% yield and characterized by a melting point m.p.=93–95° C.

$^1$H-NMR (300 MHz) (CDCl$_3$) (ppm): 2.40 (6H, s, 2CH$_3$), 2.15 (6H, s, 2CH$_3$).

c) Preparation of 4,4'-bisdiphenylphosphinoxy-2,2'5,5'-tetramethyl-3,3'-dithiophene.

5 ml of a BuLi 1,6M solution were dripped in a solution of 1.37 g of 4,4'-dibromo-2,2',5,5'-tetramethyl-3,3'-dithiophene in 25 ml of anhydrous THF, at a temperature of −15° C. during 2 minutes. After 20 minutes, 1.46 ml of diphenylchlorophosphine were dripped at 0° C., and the reaction mix was left to rest for 1 h 30 minutes. Then 100 ml of ether were added, the mix was washed with 10 ml of water and the organic phase was anydrified on sodium sulfate. The solvent was removed by evaporation under reduced pressure and 2.70 g of residue were obtained. Such residue was completely oxidized to diphosphinoxide by dissolving it in 100 ml of CH$_2$Cl$_2$ and dripping 3.6 ml of 30% hydrogen peroxide at a temperature of 0° C. After 2 hours, 15 ml of water were added and the organic phase was separated and made anhydrous on Na$_2$SO$_4$. The solvent was removed by evaporation under reduced pressure and a residue was obtained which was chromatographied on silica gel, utilizing as eluent a mix constituted by CH$_2$Cl$_2$/AcOEt/Et$_3$N 7/3/0,2 (v/v/v). The tail fractions were collected, the solvent was evaporated under reduced pressure and an oil was obtained which was treated with ethyl ether, obtaining 0.190 g of 4,4'-bisdiphenylphosphinoxide-2,2',5,5'-tetramethyl-3,3'-dithiophene.

$^1$H-NMR (300 MHz) (CDCl$_3$) (ppm): 7.60 (20H, m, aromatic), 1.95 (6H, d, CH$_3$ in 2,2'), 1.65 (6H, s, CH$_3$ in 5,5').

Such product may be resolved by crystallization of the diastereomeric salts, utilizing DBTA in THF according to a procedure analogous to that of Example 1 d).

0.7 g of a mix of diphosphinoxide and of 0.42 g of (−)-dibenzoyltartaric acid (DBTA) were hot dissolved in 20 ml of THF. After 12 hours 0.2 g of an adduct was obtained by filtration between the (−)-diphosphinoxide and the (−)-DBTA, with a melting point of 180° C. and $[\alpha]_D$=−44° C. (c=0.5, EtOH).

The adduct was treated according to the usual procedure, giving 560 mg of phosphinoxide. 0.56 g of (+)-phosphinoxide impure of (−)-phosphinoxide and 0.34 g of (+)-DBTA were hot dissolved in 40 ml of THF. After 12 hours, 0.185 g of an adduct were recovered between the (+)-diphosphinoxide and the (+)-DBTA, with m.p.=178° C. and $[\alpha]_D$=+39.5° (c=0.55, EtOH).

d) Preparation of 4,4'-bisdiphenylphosphinoxide-2,2', 5,5'-tetramethyl-3,3'-dithiophene.

0.14 ml of triethylamine and 0.10 ml of trichlorosilane were added to a solution of 0.053 g of 4,4'-bisdiphenylphosphinoxide-2,2'-5,5'-tetramethyl-3,3'-dithiophene in 5 ml of xylene, in argon atmosphere. The reaction mix was heated for 1 h at 100° C., for 1 h at 120° C. and for 6 h at 140° C. The reaction mix was treated by adding 4 ml of water and extracting with 20 ml of CH$_2$Cl$_2$. The organic phase was made anhydrous on sodium sulfate and the solvent was removed by mechanical pump evaporation, obtaining 4,4'-bisdiphenylphosphine-2,2',5,5'-tetramethyl-3,3'-dithiophene.

The resolution of the so obtained racemic diphosphine was carried out by HPLC, using a DAICEL CHIRALCEL OD (25 cm×4 mm) column, utilizing hexane/isopropanol as eluent, flow=0.7 ml/min.

EXAMPLE 3

Preparation of a complex {Ru[compound (III) R)(+)]Cl$_2$}.

A test tube provided with a side faucet, a ground cone and a teflon-covered stirring rod, was repeatedly evacuated and pressurized with argon; the operation was repeated at least 5 times. In the tail-test tube were let in, in the following order, 16.0 mg of optically pure chiral diphosphine (III R)(+)(2.3×10$^{-2}$ mmoles), 5.6 mg of [RuCl$_2$(C$_6$H$_6$)]$_2$, (1.15× 10$^{-2}$ mmoles), prepared according to the procedures reported by the literature, and 4 ml of freshly distilled in inert atmosphere dimethylformamide and argon-degased for 15 minutes. The red-brown suspension was heated at 100° C. for 15 minutes under stirring; the suspension transformed rapidly into a clear yellow-orange solution. The solution was cooled to 50° C. and evaporated to dryness. The residue was left under mechanical vacuum for one hour and afterward argon-pressurized. The so obtained Rutenium complex was utilized without further purifications in the enentioselective reduction of ketoesters.

EXAMPLE 4

Preparation of a complex {Rh[1,5-cycloctadiene][compound (III S)(−)]ClO$_4$}.

A test tube provided with a side faucet, a ground cone and a teflon-covered stirring rod, was repeatedly evacuated and pressurized with argon; the operation was repeated at least 5 times. 11.0 mg of optically pure chiral diphosphine (III S)(−)(1.59×10$^{-2}$ mmoles) were introduced in the test tube and dissolved in 10 ml of CH$_2$Cl$_2$ distilled in inert atmosphere and argon-degased for 15 minutes before the use. An excess of [Rh(1,5-COD)$_2$]ClO$_4$ was weighed and introduced in a tail-test tube, flashed and argon-pressurized; an exactly calibrated volume of CH$_2$Cl$_2$ was added, and a yellow solution was obtained. Through a syringe a volume was drawn containing exactly 1.59×10$^{-2}$ mmoles which was added to the diphosphine III solution. The solution turned rapidly to yellow-orange; the solution was left under stirring for 30 minutes and evaporated until it left a yellow-orange solid of {Rh[1,5-COD][compound (III S)(−)]ClO$_4$}. The so obtained Rhodium complex was utilized without further purifications in the enantioselective reduction of olefins.

EXAMPLE 5

Reduction of 3-oxo-ethylbutyrate to (R)-(−)-3-ethyl hydroxybutyrate.

A 75 ml stainless steel autoclave, provided with glass-liner, magnetic stirring and heating was hydrogen-pressurized several times to 4.90 MPa and evacuated (the cycle was repeated at least 5 times), and thermostated at 70° C. 2.993 g (23.0 mmoles) of 3-oxo-ethyl butyrate and 20 ml of methanol previously argon-degased for 15 minutes were added to the catalyst prepared according to the modalities described for Example 3. The solution was transferred by means of a syringe into the autoclave, which was pressurized at 9.81 MPa. After 120 minutes, the autoclave was cooled, opened, and the solvent evaporated until it left a brown oily residue. A sample was examined through GC (column PEG 20 M, oven temperature 100° C., FID 200° C., injector 200° C.) and $^1$H-NMR spectroscopy; the results showed a quantitative conversion of the substrate and a 3-ethyl-3-hydroxybutyrate selectivity equal to 95%; the by-product resulted to be ethyl-3-dimethoxybutyrate. The residue was vacuum-distilled, collecting the fraction passing between 75 and 80° C. at 17 mmHg. The obtained sample resulted to be the chemically pure hydrogenation product.

ethyl-3-hydroxybutyrate: $^1$H-NMR (200 MHz) (CDCl$_3$ (ppm): 4.2 (3H, q and m superposed), 2.4 (2H, d), 1.2 (6H, t and d superposed).

The stereoinduction was determined polarimetrically and through $^1$H-NMR spectroscopy with tris[3-(+) camphorated trifluoromethylhydroxymethylene)] Eu as shift chiral reagent. The specific rotatory power was $[\alpha]_D^{20}$=−41.5 (c=1, CHCl$_3$), corresponding to a 99% optical purity (O.P.) in favour of the R enantiomer [the literature reports for the (S)-(+) enantiomer: $[\alpha]_D^{20}$=+42±1 (c=1, CHCl$_3$); A.FISCHLI, Modern synthetic methods Vol. 2,269, 1980, R.Scheffold Publishing House, Salle+Sauerlander]. The enantiomeric excess was determined through $^1$H-NMR spectroscopy with shift chiral reagent. The addition of the shift reagent on the racemic reduction product caused the separation of the triplet positioned at 1.2 ppm into two triplets positioned at 1.40 and 1.55 ppm respectively. The addition of the same chiral reagent to the enantioselective reduction product caused the shift of the triplet at 1.4 ppm without showing in any way the presence of the triplet at 1.55 ppm. This result allowed to confirm an enantiomeric excess higher than 99%.

EXAMPLE 6
Reduction of methyl 2-oxocyclopentancarboxylate to (R,R)-(−)-methyl 2-hydroxycyclopentancarboxylate.

The preparation procedure of the apparatus was the same as that of Example 5. 3.270 g (23,0 mmoles) of methyl 2-oxocyclopentancarboxylate in 20 ml of degased methanol were added to the catalyst prepared as in Example 3, the autoclave was thermostated at 70° C. and pressurized at 9.81 MPa. After 120 minutes the autoclave was cooled, opened and the solvent evaporated until it left an oily brown residue. A sample was GC-examined (column: PEG 20 M, oven temperature 160° C., FID 200° C., injector 200° C.); the conversion resulted to be quantitative, the trans/cis ratio equal to 30 and consequently the diastereomeric excess equal to 94%. The residue was vacuum distilled, collecting the fraction passing between 100 and 110° C. at 17 mmHg. The obtained sample resulted to be the chemically pure hydrogenation product.

Methyl 2-hydroxycyclopentancarboxylate: $^1$H-NMR (200 MHz) (CDCl$_3$) (ppm): 4.35 (1H, m), 3.71 (3H, s), 2.65 (1H, m), 2.4–1.5 (6H, m). The stereoinduction was determined by $^1$H-NMR spectroscopy and trid[(+)camphorated 3-eptafluoromethylhydroxymethylen] Eu as shift chiral reagent. The addition of the shift reactant on the racemic reduction product caused the separation of the quartet positioned at 4.40 ppm into two quartets positioned at 5.2 and 5.85 ppm respectively. The addition of the same chiral reagent to the stereoselective reduction product caused the shift of the quartet at 5.85 ppm without showing in any way the presence of the quartet at 5.2 ppm. This result allowed to confirm an enantiomeric excees higher than 99%.

EXAMPLE 7
Reduction of α-acetamidocinnamic acid.

A 100 ml glass autoclave provided with magnetic stirring was pressurized several times at 98.1 KPa with hydrogen and evacuated (the cycle was repeated at least 5 times) and thermostated at 30° C.; 500 mg of α-acetamidocinnamic acid (2.06 mmoles) dissolved in 40 ml methanol, previously argon-degased for 15 minutes, were added to the catalyst prepared according to the description of Example 4; the solution obtained was transferred into the autoclave through a syringe. The autoclave was pressurized at 0.3 MPa. The reaction process was followed through the manometer pressure drop. After 180 minutes, the hydrogen absorption stopped, the autoclave was opened and a sample of the solution was analyzed by $^1$H-NMR spectroscopy. The disappearance of the signal of the substrate acetyl group at 2.1 ppm and the appearance of the methyl group of the N-acetylphenylalanine at 1.90 ppm indicated a 100% conversion. The solution was filtered through a short silica column to eliminate the Rhodium complex. The stereoselection was determined polarimetrically. A sample of the residue (0.211 g), dissolved in 25 ml of methanol gave an α=+0.193° corresponding to an $[\alpha]_D^{25}$=+22,9°.

EXAMPLE 8
Preparation of the chiral diphosphines (VI R) and (VI S).
a) Preparation of N-(phenylsulphonyl)-3-methylindole.

50% sodium hydride (1.1 g) was added to a solution of 3-methylindole (4 g) dissolved in anhydrous DMF (50 ml), keeping the temperature under 30° C. Stir for 15 minutes, then drip carefully the phenylsulphonyl chloride (4.7 ml) dissolved in anhydrous DMF (20 ml) and leave under stirring for 2 hours at 25° C. Then add methanol (5 ml) to decompose the possible present traces of BuLi; remove the solvent under reduced pressure, add water (20 ml) and extract exhaustively with methylenchloride. The organic phase is made anhydrous on sodium sulfate and the solvent is removed under reduced pressure. The residue (9.5 g) is ground in methylenchloride/hexane 1:1 to obtain N-(phenylsulphonyl)-3-methylindole (2 g) (m.p. 116–120° C.). The mother liquors are chromatographied to recover more product, eluting with methylenchloride/hexane 1:1. N-(phenylsulphonyl)-3-methylindole (7 g) is recovered from the intermediate fractions, removing the solvent under reduced pressure.

Total reaction yield: 85%. $^1$H-NMR details: 7.99 (1H, d, J=8 Hz, H in position 7): 7.86 (1H, d, J=8 Hz, H in ortho position on phenyl ring); 7.38 (6H, m, aromatic); 7.31 (1H, s, H in position 2); 2.25 (3H, s, CH$_3$ in position 3).
b) Preparation of N,N'-bis(phenylsulphonyl)-3,3'-dimethyl-2,2'-biindole.

1.6 M (61 ml) of BuLi are dripped in a solution of N-phenylsulphonyl-3-methylindole (30 g) and TMEDA (100 ml) in anhydrous THF (10 ml) kept at −30° C. Stir for 30 minutes at the same temperature, add the anhydrous cupric chloride (13 g) and leave to rest at room temperature in 1 hour. The solvent is removed under reduced pressure, then add water (50 ml) and extract exhaustively with methylene chloride. The organic phase is made anhydrous on sodium sulfate and the solvent is removed under reduced pressure.

The residue is hot ground in isopropanol to obtain N,N'-bis (phenylsulphonyl)-3,3'-dimethyl-2,2'-biindole (6 g) (m.p. 224° C.).

$^1$H-NMR details: 8.35 (2H, d, J=8 Hz, H in position 7 and 7'); 7.48 (10H, m, aromatic); 7.3 (6H, m, aromatic); 1.62 (6H, s, CH$_3$ in position 3 and 3'). Mass spectrometry (e.i.): (M$^+$) 540.

The filtrate is cold ground with isopropanol, recovering the unreacted N-phenylsulphonyl-3-methylindole (8 g). The mother liquors are chromatographied on silica gel, eluting with methylenchloride/hexane 1:1. The head fractions supply N-phenylsulphonyl-3-methylindole (7 g). The tail fractions are collected and freed from the solvent, to produce N,N'-bis (phenylsulphonyl)-3,3'-dimethyl-2,2'-biindole (4.5 g).

Preparation of 2-[2-(3-methyl-3-hydroxy)-delta$^1$-indolinyl]-3-methylindole.

A suspension of N,N'-bis(phenylsulphonyl)-3,3'-dimethyl-2,2'-diindole (10 g), potassium hydroxide (8.3 g), dioxane (80 ml) in ethanol (300 ml) is refluxed for 5 hours and then freed from the solvent. The reaction mix is treated with water and exhaustively extracted with methylenchloride. The organic phase is made anhydrous on sodium sulfate and the solvent is removed under reduced pressure. The obtained mix is left under aeration-stirring for 24 hours in methylenchloride and the starting product is recovered by filtration. The solid corresponds to 2-[2-(3-methyl-3-hydroxi)-delta$^1$-indolinyl]-3-methylindole (2 g) (m.p. 94° C.).

$^1$H-NMR details: 9 (1H, s, NH); 7.52 (1H, d, J=7.9 Hz, H in position 4'); 7.29 (1H, d, J=5.6 Hz, H in position 7); 7.14 (1H, t, J=7.9 Hz, H in position 6'); 7 (5H, m, aromatic); 1.52 (3h, s, CH$_3$ near OH).

The mother liquors are chromatographied, eluting with methylenchloride and afterwards with methylenchloride/ethylacetate 10:0.1. The 2-[2-(3-methyl-3-hydroxydelta$^1$indolinyl]-3-methylindole (0,7 g) is recovered from the tail fractions, removing the solvent under reduced pressure.

d) Preparation of 3,3'-dimethyl-2,2'-diindole.

The 2-[2-(3-methyl-3-hydroxy)-delta$^1$-indolinyl]-3-methylindole (2,5 g) is hot dissolved in ethanol under nitrogen-aeration to remove any trace of oxygen left. Sodium borohydride (0.51 g) dissolved in the minimun quantity of water (10 ml) is dripped and left under stirring for 2 hours at 25° C. A 10% hydrochloric acid solution is dripped to obtain a pH 6 and left under stirring for 12 hours. The residue is filtered under nitrogen, to produce 3,3'-dimethyl-2,2'-diindole (m.p. 146–149° C. as quantitative yields.

$^1$H-NMR details: 8 (2H, s, broaded, NH); 7.63 (2H, d, J=8 Hz, H in position 4 and 4'); 7.39 (2H, d, J=8 Hz, H in position 7 and 7'); 7.25 (2H, t, J=8 Hz, H in position 5 and 5'); 7.18 (2H, t, J=8 Hz, H in position 5 and 5'); 2.40 (6H, s, CH$_3$ in position 3 and 3+).

e) Preparation of N,N'-bis(diphenylphosphin)-3,3'-dimethyl-2,2'-diindole.

1.6M (1.1 ml) of BuLi are dripped in a solution of 3,3'-dimethyl-2,2'-diindole (0.24 g) in anhydrous THF (85 ml) kept at –20° C. and well degased, and after 2 minutes the diphenylchlorophosphine (0.4 g) dissolved in anhydrous THF (5 ml) is dripped.

Keep under stirring for 16 hours, remove the solvent under reduced pressure and add water (20 ml). Extract exhaustively with methylenchloride, make anhydrous on sodium sulfate and remove the solvent under reduced pressure. The residue is chromatographied on silica gel, eluting with hexane/methylene chloride 8:2; a residue is recovered from the head fractions, which residue, ground in isopropanol, produces N,N'-bis(diphenylphosphine)-3,3'-dimethyl-2,2'-diindole (m.p.>230° C.), with a 95% yield.

$^1$H-NMR details: 7.59 (2H, d, J=8 Hz, H in position 4 and 4'); 7.3 (14H, m, aromatic); 7.1 (6H, m, aromatic); 6.85 (2H, t, J=5, H in position 6 and 6'); 6.7 (2H, d, J=8 Hz, H in position 7 and 7'); 2.05 (6H, s, CH$_3$ in position 3 and 3'). $^{31P}$P-NMR details: 37 (1P, s). Mass spectrometry (e.i.): (M$^+$) 628.

f) Preparation of N,N'-bis(diphenylphosphinyl)-3,3'-dimethyl-2,2'-diindole.

35% H$_2$O$_2$ (0.16 ml) is dripped in a solution of N,N'-bis (diphenylphosphin)-3,3'-dimethyl-2,2'-diindole (0.1 g) in CH$_2$Cl$_2$ (5 ml) at –30° C. The temperature is kept at –30° C. for 2 hours. Water is added and the organic phase is separated, which phase is anydrified and freed from the solvent under reduced pressure to produce racemic N,N'-bis-diphenylphosphinyl-3,3'-dimethyl-2,2'-diindole (0.1 g).

$^1$H-NMR details: 1.8 (6H, s, 2CH$_3$ in position 3 and 3'); 7.1 (28H, m, aromatic).

g) Resolution of 1,1'-bis(diphenylphosphinyl-3,3+-dimethyl-2,2'-diindole.

0.28 g of a mix of diphosphinoxide and 0.21 g of d-10-camphosulfonic acid were hot dissolved in 9 ml of a mix constituted by toluene/CH$_2$Cl$_2$ 8:1 (v/v). After 60 hours, 78 mg of an adduct were obtained between the diphosphinoxide and the d-10-camphosulfonic acid, with a melting point=125–127° C. and [α]$_D$=+34° (c=1.56, MeOH).

The reduction of the diphosphinoxide was realized in the same way as described for Example 1 g).

EXAMPLE 9

Preparation of chiral diphosphines (VII R) and (VII S).

a) Preparation of 3,3'-dibenzo[b]thiophene.

The 3-bromo-benzo[b]thiophene (15.1 g) dissolved in anhydrous THF (40 ml) is dripped under stirring in a solution of n-BuLi 1.6 M (48 ml) at –70° C. Let react for 15 minutes, add CuCl$_2$ (13 g) and leave under stirring for 1 hour. Raise the temperature to 0° C. and add HCl 2M (98 ml). The organic salts which have formed are removed by filtration, the solvent is distilled under reduced pressure and water is added to the residue. Extract with CH$_2$Cl$_2$, make anhydrous with Na$_2$SO$_4$ and distillate the solvent under reduced pressure. The residue is chromatographied on silica gel, using hexane as eluent and the intermediate fractions are collected to produce 3,3'-dibenzo[h]thiophene (56% yield). $^1$H-NMR: 7.38 (4H, m, H in 5, 6, 5', 6'); 7.55 (2H, s, H in 2); 7.72–7.98 (4H, m, H in 4, 7, 4' and 7').

b) Preparation of 2,2'-bis-(diphenylphosphin)-3,3'-dibenzo [b]thiophene.

1.6 M (8.4 ml) of n-BuLi are dripped, in nitrogen atmosphere and under stirring, in a solution of 3,3'-dibenzo[b] thiophene (1.7 g) and tetramethylendiamine (1.15 ml) in anhydrous THF (40 ml), at –50° C., and the temperature is raised to 0° C. Ph$_2$PCl (2.4 ml) is dripped and left to rest at room temperature. Distillate the solvent under reduced pressure, add water to the residue and then extract with CH$_2$Cl$_2$. The organic phase is made anhydrous with Na$_2$SO$_4$ and freed from the solvent under reduced pressure. The residue is ground with petroleum ether to produce 2,2'-bis (diphenylphosphin)-3,3'-dibenzo[b]thiophene (3.12 g, m.p.= 177° C.) (99% yield).

c) Preparation of 2,2'-bis-(diphenylphosphinyl)-3,3'-dibenzo [b]thiophene.

35% H$_2$O$_2$ (5.5 ml) is dripped in a solution of 2,2'-bis (diphenylphosphin)-3,3'-dibenzo[b]thiophene (3.49 g) in CH$_2$Cl$_2$ (100 ml) at 0° C. The temperature is kept at 0° C. for 1 hour and at 25° C. for 1 hour. Add water and separate the organic phase which is made anhydrous and freed from the solvent under reduced pressure. The residue is chromatographied on silica gel (eluent AcOEt/CH$_2$Cl$_2$/Et$_3$N 3/7/ 0,1), collecting the tail fractions to produce the racemic 2,2'-bis (diphenylphosphinyl)-3,3'-dibenzo[b]thiophene (3.65 g, m.p.=286° C.) (68.5% yield)

d) Preparation of (+) 2,2'-bis(diphenylphosphinyl)-3,3'-dibenzo[b]thiophene and (–) 2,2'-bis(diphenylphosphinyl)-3,3'-dibenzo[b]thiophene.

A mix of (±) 2,2'-bis(diphenylphosphinyl)-3,3'-dibenzo [b]thiophene (2.15 g) and of (–)-O,O'-dibenzoyl-L-tartaric acid (DBTA) (1.2 g) is hot dissolved with a solution of AcOEt (90 ml) and CHCl$_3$ (43 ml). After 24 hours, an adduct is recovered by filtration between the (+)phosphinoxide and the (–)-DBTA (0.54 g) with m.p.=185–190° and [α]$_D^{25}$=+ 100,6° (c=0.50, EtOH). The adduct is filtered on a column of silica gel, utilizing as eluent a mix of CH$_2$Cl$_2$AcOEt/ TEA=7/3/0,1, and the (+)-phosphinoxide (0.212 g) is recovered with [α]$_D^{25}$=+325° (c=0.48, benzene) and m.p.=206° C.

The mother liquors of the resolution of the (+)-phospinoxide are freed from the solvent under reduced pressure to produce a residue which is filtered on a column of silica gel, using as eluent a mix CH$_2$Cl$_2$AcoEt/TEA=7/

3/0,1. The (−)-phosphinoxide, impure of (+)-phosphinoxide, (6 g) is recovered and treated with (+)-DBTA (3.4 g). The mix is hot dissolved with a solution constituted by AcOEt (255 ml) and CHCl$_3$ (147 ml). After 24 hours, the adduct is recovered by filtration between the (−)phosphinoxide and the (+)-DBTA (4 g) with $[\alpha]_D^{25}$=−97.4° (c=0.47), EtOH) and m.p.=190° C. The adduct is filtered on silica gel column, utilizing as eluent a mix of CH$_2$Cl$_2$AcOEt/TEA=7/3/0.1, and the (−)-phosphinoxide (2,7 g) is recovered with $[\alpha]_D^{25}$=−329° (c=0.5, benzene) and m.p.=206° C.

e) Preparation of (+) 2,2'-bis(diphenylphosphine)-3,3'-dibenzo[b]thiophene and (−) 2,2'-bis (diphenylphosphin)-3,3'-dibenzo[b]thiophene.

The reduction of the diphosphinoxide has been realized in the same way as described for Example 1, point g).

The diphosphine (+) is characterized by a value of $[\alpha]_D^{25}$=+119° C. (c=0.51, DMF), while the diphosphine (−) is characterized by a value of $[\alpha]_D^{25}$=−119° C. (c=0.51, DMF). The product has a melting point=117° C.

EXAMPLE 10

Preparation of (R) and (S) 2,2'-bis(diphenylphosphin)-1,1'-dibenzoimidazole.

a) Preparation of 1,1'-dibenzoimidazole.

200 ml of a solution of potassium permanganate (1.6 g) are dripped in a suspension of 2,2'-diphormyl-1,1'-dibenzoimidazole (3.00 g) in water (200 ml), benzene (70 ml) and 1.12 g of sodium carbonate. The mix is left under stirring for 48 hours. Sodium bisulfite is added until the manganese bioxide disappears, then the solution is brought to an acid pH with a 10% solution of hydrochloric acid and the organic phase is extracted with methylene chloride, anhydrified with sodium sulfate and freed from the solvent under reduce pressure to produce a residue which is crust-freed with isopropyl ether, supplying 1.5 g of product with m.p. 188° C. (61.7% yield).

$^1$H-NMR: 7.02 (2H, d, in position 4 and 4'); 7,3–7,5 (4H, m, in position 5 and 5', 6 and 6'); 7.92 (2H, d, in position 7 and 7'); 8.17 (2H, s, in position 2 and 2'). M.W. (Mass spectometry): 294.

b) Preparation of 2,2'-bis(diphenylphosphin)-1,1'-dibenzoimidazole.

9.4 ml of 1.6 M BuLi are dripped, at −60° C. and in inert atmosphere, in a solution of 1,1'-dibenzoimidazole (1,5 g) in anhydrous THF (70 ml) and 2.25 ml of TMEDA. The temperature is raised to 0° C. and 2.78 ml of chlorodiphenylphosphine are dripped. The reaction mix is left under stirring for 2 hours, the temperature is brought to 20° C. and methanol is added. The mix is freed from the solvent under reduced pressure and the residue is treated with water and methylen chloride. The organic phase, made anhydrous with sodium sulfate and freed from the solvent under reduced pressure produced a residue which is crystallized by ethyl acetate (3.00 g in 450 ml), supplying the product with m.p.=227° C. (78% yield).

$^1$H-NMR: 6.3 (2H, d, H in position 7 and 7'); 6.93 (2H, t, H in position 6 and 6'); 7.11–7.39 (20H, m, aromatics in para and meta position and hydrogens in position 5 and 5'); 7.51–7.59 (2H, m, aromatic in ortho position); 7.88 (2H, d, aromatic in position 4 and 4'). The spectrum $^{31}$P NMR shows a singlet at −28.3 ppm. M.W. (mass spectrometry): molecular peak absent. 525 (M$^+$-C$_6$H$_5$).

c) Resolution of the diphosphine.

The resolution of the racemic diphosphine was performed by HPLC in the same way as for Example 2, point d).

EXAMPLE 11

Preparation of [Ru {compound III S)}(−)]Cl$_2$].

The preparation is analogous to that of example 3, but utilizing 37.0 mg of [(III S) (−)] and 13.0 mg of [RuCl$_2$(C$_6$H$_5$)]$_2$.

EXAMPLE 12

Reduction of methyl benzoylacetate to methyl (R)-(+)-3-phenyl-3-hydroxy-propionate.

A 75 ml stainless steel autoclave, provided with glass-liner, magnetic stirring and heating was pressurized several times to 4.90 Mpa with hydrogen and evacuated (the cycle is repeated at least 5 times) and thermostated at 25° C. 9.25 g (52 mmoles) of methyl benzoylacetate dissolved in 50 ml of methanol previously argon-degased for 15 minutes were added to the catalyst prepared according to the modalities described for Example 11.

The solution was transferred by means of a syringe into the autoclave which was pressurized at 10.2 MPa. After 100 hours, the autoclave was depressurized and the solvent was evaporated, leaving a solid. The conversion, equal to 92%, was determined by $^1$H-NMR spectrometry on a sample.

The reaction product was purified by preparative column chromatography (SiO$_2$, CH$_2$Cl$_2$). The enantiomeric purity was determined polarimetrically. A sample of the product gave a specific rotatory power $[\alpha]_D$=+15.3 (c=4.6, EtOH) corresponding to a 90% optical purity in favour of the (R)-(+) isomer. ($[\alpha]_D^{25}$=+17.22 (c=4.6, EtOH); [A. McKenzie and G. Martin, J.Chem.Soc., 1913, 103, 112]).

EXAMPLE 13

Reduction of methyl phenylglyoxylate to produce (S)-(+)-methyl mandelate.

The procedure of Example 12 was repeated, substituting methyl phenylglyoxylate (8.5 g, 51.8 mmoles) for methyl benzoylacetate.

After 100 hours the autoclave was opened and the solvent evaporated. The conversion resulted to be 90% ($^1$H-NMR). The chemicaly pure methyl mandelate was obtained by column chromatography (SiO$_2$, hexane/CH$_2$Cl$_2$ 7/3 v/v). The enantiomeric purity was determined through HPLC on chiral stationary phase (DAICEL, Chiralcel OD; flow 0.5 ml/min, hexane/isopropanol 90:10) and resulted to be equal to 90% in favour of the enantiomer (S)-(+).

EXAMPLE 14

Reduction of methyl pyruvate to (S)-(−) methyl lactate.

The procedure of Example 12 was repeated, substituting methyl pyruvate (3.13 mg, 30.74 mmoles) for the methyl benzoylacetate.

After 100 hours the conversion resulted to be equal to 100% ($^1$H-NMR), the solvent was evaporated and the methyl lactate was distillated (50° C., 17 mmHg). After transformation of the methyl lactate into the corresponding ester of the (+) MTPA, according to the normal procedures, the e.e. was determined by HPLC analysis and resulted to be 88% in favour of the enantiomer (S).

EXAMPLE 15

Preparation of [Ru[(compound VII S) (−)]Cl$_2$].

The preparation is the same as that of Example 11, but utilizing 10.6 mg of [(VII S) (−)] and 3.7 mg of [RuCl$_2$(C$_6$H$_5$)]$_2$.

EXAMPLE 16

Reduction of ethyl 3-oxobutyrate to (S) (+) ethyl 3-hydroxybutyrate.

The same procedure of Example 5 is repeated with the only differences that 1.95 g of ethyl 3-oxo-butyrate were weighed and dissolved in MeOH/H$_2$O 19/1 (v/v) and the catalyst of Example 15 was utilized. At the end of the reaction, the ethyl 3-hydroxybutyrate resulted to be equal to 91%, while the ethyl 3-dimetoxybutyrate resulted equal to 9%. The stereoinduction was >99% in favour of the antipode (S).

EXAMPLE 17

Preparation of [Ru(compound III S) (−) (CH$_3$COO)$_2$].

The [Ru[(compound III S) (−)]Cl$_2$] complex was prepared as for Example 11, but utilizing 47 mg of [(III S) (−)] and 17 mg of [RuCl$_2$(C$_6$H$_5$)]$_2$. 22.7 mg of silver acetate and 7 ml of anhydrous toluene were added to the so obtained residue. The suspension was left under stirring for 1 hour and afterwards filtered on a short column of microcrystalline cellulose, washing with more toluene to elute all the catalyst. The toluenic solution comprising [Ru[(compound III S) (−)](CH$_3$COO)$_2$], kept under Ar atmosphere, was used in catalitic reductions without further purifications.

EXAMPLE 18

Reduction of geraniol to (R)-(+)-β-citronellol.

A sample of toluenic solution containing 0.015 mmoles of the catalyst prepared as in Example 17 was evaporated to dryness, 889 mg of geraniol and 10 ml of methanol were added to the residue. The resulting solution was transferred into a steel autoclave and the autoclave was pressurized at 10.2 MPa, kept under stirring for 85 hours in a bath thermostated at 25° C.

At the end, the autoclave was opened and the solvent evaporated. The conversion resulted to be 100% ($^1$H-NMR).

The residue was bulb-to-bulb distilled (110° C., 10 mm Hg). The specific rotatory power of (R)-(+)-β-citronellol resulted to be [α]$_D^{25}$=+4.44 (neat), producing an optical purity equal to 83% ([α]$_D^{25}$=+5.33, neat).

EXAMPLE 19

Reduction of tiglyc acid to (S)-(+)-2-methylbutyric acid.

The same procedure as for Example 18 was repeated, with the difference that 600 mg of tiglyc acid, instead of geraniol, were utilized.

The autoclave was pressurized at 1.02 MPa, placed in a bath thermostated at 25° C. and left under magnetic stirring for 85 hours.

After the usual work-up, a 100% conversion was obtained ($^1$H-NMR). The product was bulb-to-bulb distilled (78° C., 15 mmHg). The enantiomeric purity was determined through HPLC on chiral stationary phase (DAICEL, Chiralcel OD; flow 0.7 ml/min, hexane/isopropanol 95/5) on the amide obtained by condensation of the acid with aniline and resulted to be equal to 90%.

EXAMPLE 20

Reduction of atropic acid to (S)-(+)-2-phenylpropionic acid.

The same procedure as for Example 18 was repeated, with the difference that 742 mg of atropic acid, instead of geraniol, were weighed. The autoclave was pressurized at 10.2 MPa, placed in a bath thermostated at 25° C. and left under magnetic stirring for 90 hours.

After the usual work-up a 100% conversion was obtained ($^1$H-NMR). The produce was bulb-to-bulb distilled (115° C., 1 mmHg). The enantiomeric purity was determined through HPLC on chiral stationary phase (DAICEL, Chiralcel OD; flow 0.5 ml/min, hexane/isopropanol 90/10) on the amide obtained by condensation of the acid with aniline and resulted to be 90% in favour of the enatiomer (S)-(+).

EXAMPLE 21

Preparation of [Rh[(compound III S) (−)]$_2$]ClO$_4$.

1,1 ml of a 0.0424 M solution of AgClO$_4$ in anhydrous toluene were added in argon-atmosphere in a tail-test tube containing 11.6 ml of [Rh(1,5-COD)Cl]$_n$. After 1 h at room temperature under stirring, the mix was filtered through a short celite column and 32.5 mg of (compound III S) (−) were added to the so obtained pale yellow solution. The solution was left under stirring for 3 h, and then 32.5 mg of (compound III S) (−) were furtherly added. The mix was kept under stirring for other 16 h in hydrogen atmosphere, then evaporated under reduced pressure and the orange-red residue was washed three times with petroleum ether and vacuum-dried overnight. The complex [Rh[(compound III S) (−)]$_2$]ClO$_4$ so formed was utilized without further purifications in the isomerization of the N,N-diethylgeranylamine. The NMR and mass spectra and the elementary analysis of the complex were conform to the aforementioned structure.

EXAMPLE 22

Isomerization of N,N-diethylgeranilamine. Preparation of (R) (+) citronellal.

A solution of 15 mg of [Rh[(compound III S) (−)]$_2$]ClO$_4$ prepared as described in the preceding Example 21 in 3 ml of anhydrous THF and a solution of 0.99 g of N,N-diethylgeranilamine in 12 ml of THF were transferred by means of a syringe into an autoclave preliminarily conditioned in argon-atmosphere. The autoclave was placed in a bath thermostated at 110° C. under magnetic stirring. After 9 h a sample of solution (1 ml) was taken, diluited with 9 ml of diisopropylether and treated for 10' at 0° C. with 5 ml of a 1:4 solution of glacial acetic acid/water (v/v). After other 10' at 20° C., the organic phase was separated and washed with a saturated solution of NaHCO$_3$, made anhydrous on sodium sulfate and GC-analyzed. The conversion resulted to be of about 80%. After 10 further hours of reaction the solution was concentrated to dryness and processed as described above, utilizing 20 ml of diisopropyl ether and 10 ml of a 1:4 solution of glacial acetic acid/water (v/v). Lastly, the organic phase was concentrated and the residue distilled to obtain (R) (+) citronellal having a specific rotatory power of [α]$^{25}$ +15.2 (neat) corresponding to an optical purity of about 92%.

EXAMPLE 23

Preparation of 2,2'-bis(diphenylphosphinyl)-4,4'-tetramethyl-3,3'-[b]furan.

a) Ethyl 2-(3,5-dimethylphenyloxy) acetate.

A solution of 3,5-dimethylphenol (0.082 moles) in methanol (30 ml) was dripped in a solution of sodium methylate (0.098 moles) in methanol and left under stirring for 30 minutes. The mix was freed from the solvent under reduced pressure to produce sodium 3,5-dimethylphenate. The ethyl 2-bromoacetate (0.098 moles) dissolved in DMF (20 ml) was dripped in the solution obtained by dissolving the salt in anhydrous DMF (150 ml). The mix was stirred at room temperature for 4 hours, then freed from the solvent under reduced pressure, treated with water and extracted with methylene chloride. The organic phase was separated, made anhydrous (Na$_2$SO$_4$) and freed from the solvent under reduced pressure to produce 22.7 g of crude ethyl 2-(3,5-dimethylphenoxy) acetate, which is utilized for the subsequent reaction without further purifications (quantitative yield).

Analytic and spectroscopic details.

$^1$H-NMR: $\delta_H$(300 MHz, CDCl$_3$) 1.28 (3H, t, CH$_2$CH$_3$), 2.25 (6H, s, 3,5-Me), 4.25 (2H, q, CH$_2$CH$_3$), 4.5 (2H, s, CH$_2$CO), 6.5 (2H, s, 2,6-H), 6.6 (1H, s, 4-H).

b) 2-(3,5-dimethylphenoxy) acetic acid.

KOH (0.11 moles) is added to a solution of ethyl 2-(3,5-dimethylphenoxy) acetate (0.11 moles) in ethanol (159 ml) and heated to deposition for one hour. The potassium salt formed is filtered and dissolved in water. 20% hydrochloric acid is added to the solution until and acid pH is obtained. The 2-(3,5-dimethylphenoxy) acetic acid is filtered (80% yield).

Analytic and spectroscopic details.

m.p. 73° C.

$^1$H-NMR $\delta_H$ (80 MHz, CDCl$_3$) 2.30 (6H), s, 3,5-Me), 4.65 (2H, s, CH$_2$CO), 6.55 (2H, s, 2,6-H), 2.65 (1H, s, 4-H).

c) 4,6-dimethyl-3-benzofuranone.

A mix of polyphosphoric acid and 2-(3,5-dimethylphenoxy) acetic acid was heated at 50° C. for 8 hours. The mix was poured in ice, treated with ammonia until a pH 7 was obtained. The mix was extracted with methylenechloride and the organic phase was treated with a solution of bicarbonate, made anhydrous (Na$_2$SO$_4$) and freed from the solvent under reduced pressure, to produce 4,6-dimethyl-3-benzofuranone (40% conversion, 100% yield).

Analytic and spectroscopic details.

m.p. 55–60° C.

$^1$H-NMR $\delta_H$(80 MHz, CDCl$_3$) 2.25 (3H, s, Me), 2.45 (3H, s Me), 4.40 (2H, s, CH$_2$), 6.50 (1H, s, aromatic), 6.60 (1H, s, aromatic).

d) 4,6-dimethyl-3-bromobenzofuran.

4,6-dimethyl-3-benzofuranone (0.09 moles) was slowly added in phosphorus tribromide (30 ml), previously heated to 100° C. The mix is cautiously treated with ice, extracted with methylenechloride. The organic phase is made anhydrous (Na$_2$SO$_4$) and freed from the solvent under reduced pressure to produce 4,6-dimethyl-3-bromobenzofuran (60% yield).

Analytic and spectroscopic details.

$^1$H-NMR $\delta_H$ (80 MHz, CDCl$_3$) 2.40 (3H, s, Me), 2.70 (3H, s, Me), 6.85 (1H, s, 5-H), 7.15 (1H, s, 7-H), 7.50 (1H, s, 2-H).

e) 4,4',6,6'-tetramethyl-3,3'-bibenzo[b]furan.

4,6-dimethyl-3-bromobenzofuran (0.012 moles) dissolved in anhydrous THF (20 ml) are dripped under stirring in a solution of n-BuLi 1,6 M (9 ml) in hexane at −105° C. The mix was reacted for 20 minutes, CuCl$_2$ (0.014 moles) was added and the mix was stirred for 3 hours. At 0° C. HCl 2 M (20 ml) was added. The solvent was distilled under reduced pressure and water was added to the residue. After extraction with CH$_2$Cl$_2$, the mix was made anhydrous (Na$_2$SO$_4$) and the solvent was distilled under reduced pressure. The residue is chromatographied on silica gel using hexane as eluent, and the tail fractions are collected to obtain 4,4',6,6'-tetramethyl-3,3'-bibenzo[b]furan (30% yield).

Analytic and spectroscopic details.

m.p. 98–100° C.

$^1$H-NMR $\delta_H$ (80 MHz, CDCl$_3$) 2.10 (6H, s, Me), 2.45 (6H, s, 2Me), 6.85 (2H, s, 5,5'-H), 7.18 (2h, s, 7,7'-H), 7.50 (2H, s, 2,2'-H).

Mass spectroscopy: M$^+$=290.

f) 2,2'-bis(diphenylphosphin)-4,4',6,6'-tetramethyl-3,3'-[b]furan.

n-BuLi 1.6 M (2 ml) is dripped, under nitrogen atmosphere and under stirring, in a solution of 4,4',6,6'-tetramethyl-3,3'-bibenzo[b]furan (0.0014 mmoles) and tetramethylendiamine (0.5 ml) in anhydrous THF (10 ml), at −50° C., and the temperature is then raised to 25° C. Ph$_2$PCl (0.63 ml) was dripped. The solvent was distilled under reduced pressure, water was added to the residue and the organic phase was extracted with CH$_2$Cl$_2$. The organic phase is made anhydrous (Na$_2$SO$_4$) and freed from the solvent under reduced pressure. The residue is ground with petroleum ether to produce 2,2'-bis(diphenylphosphin)-4,4', 6,6'-tetramethyl-3,3'-[b]furan (60% yield).

Analytic and spectroscopic details.

$^1$H-NMR $\delta_H$ (300 MHz, CDCl$_3$) 1.90 (6H, s, 2Me), 2.40 (6H, s, 2me), 6.75 (2H, s, 5,5'-H), 7.80 (22H, m, aromatics).

$^{31}$P $\delta_H$ (200 MHz, CDCl$_3$) −32.15

Mass spectroscopy: M$^+$=658.

g) 2,2'-bis(diphenylphosphinyl)-4,4',6,6'-tetramethyl-3,3'-[b]furan.

35% H$_2$O$_2$ (5.5 ml) is dripped in a solution of 2,2'-bis(diphenylphosphin)-4,4',6,6'-tetramethyl-3,3'-[b]furan (0.45 g) in CH$_2$Cl$_2$ (30 ml) at 0° C. The temperature is kept at 0° C. for 15 minutes and at 25° C. for 1 hour. Water was added, the organic phase was separated, made anhydrous and freed from the solvent under reduced pressure. The residue was chromatographied on silica gel (eluent: AcOEt/CH$_2$Cl$_2$=⅔), collecting the tail fractions to produce the racemic 2,2'-bis (diphenylphosphinyl)-3,3'-bibenzo[b]thiopene (90% yield).

Analytic and spectroscopic details.

$^1$H-NMR $\delta_H$ (300 MHz, CDCl$_3$) 1.80 (6H, s, 2Me), 2.20 (6H, s, 2Me), 6.35 (2H, s, 5,5'-H), 7.00–7.80 (22H, m, aromatics).

$^{31}$P=+16.9

The resolution was carried out in the same way as in Example 2 point d) by HPLC on a chiral column.

What is claimed is:

1. Chiral catalyst for stereocontrolled synthesis comprising a complex between a transition metal and a chiral diphosphine constituted by an aromatic pentatomic biheterocyclic ring system where said chiral diphosphine is constituted by an aromatic pentatomic biheterocyclic system having the following formula:

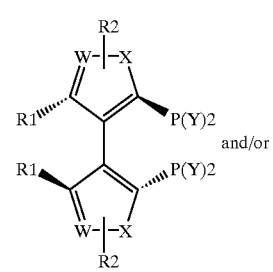

(IA)

and/or

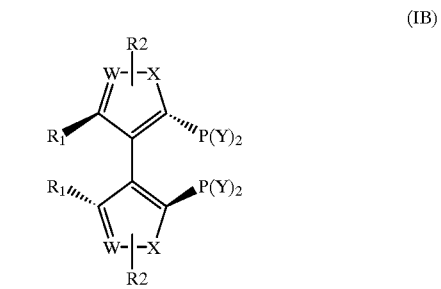

(IB)

where X is C or S; W is C or S; and with the proviso that only one of X or W is S;

where R$_2$ is selected from the group consisting of hydrogen, phenyl, aryl, linear, branched, or cyclic alkyl C$_1$–C$_{10}$, COOR$_3$, where R$_3$ is linear, branched, or cyclic alkyl C$_1$–C$_{10}$;

Y is selected from the group consisting of phenyl, substituted phenyl where substituents are selected from the group consisting of linear, branched, or cyclic alkyl $C_1-C_{10}$, halogen $OR_6$ where $R_6$ is linear, branched, or cyclic alkyl $C_1-C_{10}$, aryl, substituted aryl where substituents are selected from the group consisting of linear, branched, or cyclic alkyl $C_1-C_{10}$, halogen, $OR_6$ where $R_6$ is linear, branched, or cyclic alkyl $C_1-C_{10}$, linear branched, or cyclic alkyl $C_3-C_{10}$;

$R_1$ is selected from the group consisting of phenyl, substituted phenyl where substituents are selected from the group consisting of linear, branched, or cyclic alkyl $C_1-C_{10}$, halogen, $OR_6$ where $R_6$ is linear, branched, or cyclic alkyl $C_1-C_{10}$, aryl, substituted aryl where substituents are selected from the group consisting of linear, branched, or cyclic alkyl $C_1-C_{10}$, halogen, $OR_6$ where $R_6$ is linear, branched, or cyclic alkyl $C_1-C_{10}$, linear, branched, or cyclic alkyl $C_1-C_{10}$, $OR_5$, where $R_5$ is linear, branched, or cyclic alkyl $C_1-C_{10}$, or each pentatomic heterocyclic aromatic ring of said system is optionally fused to an optionally substituted benzene or naphthalene ring, wherein the optional substituents are selected from among the group consisting of linear, branched, or cyclic alkyl $C_1-C_{10}$, halogen, $OR_6$ where $R_6$ is linear, branched, or cyclic alkyl $C_1-C_{10}$, or unsubstituted according to the following formula:

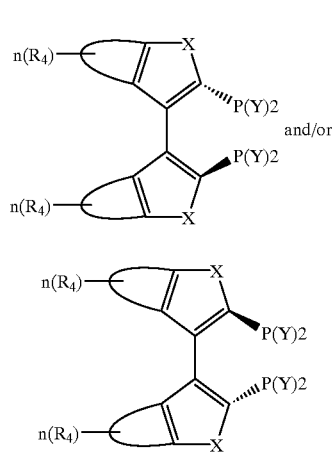

(IIA)

and/or (IIB)

where X is S;

or according to the following formula:

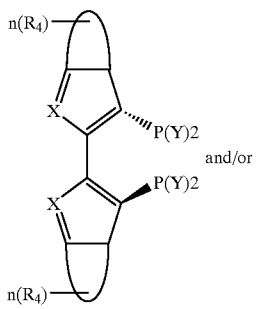

(VA)

and/or (VB)

where $R_4$ is selected from the group consisting of hydrogen, linear, branched, cyclic, or unsubstituted alkyl $C_1-C_{10}$, n ranges from 0 to 6.

2. Chiral catalyst for stereocontrolled synthesis comprising a complex between a transition metal and a chiral diphosphine constituted by an aromatic pentatomic biheterocyclic ring system where said chiral diphosphine is constituted by an aromatic pentatomic biheterocyclic system having the following formula:

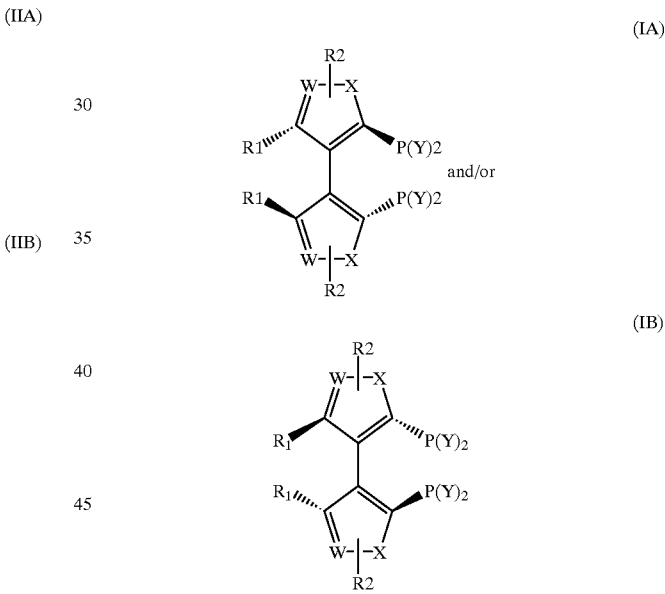

(IA)

and/or (IB)

where X is N or S; W is N or S; and with the proviso that only one of X or W is S;

where $R_2$ is selected from the group consisting of hydrogen, phenyl, aryl, linear, branched, or cyclic alkyl $C_1-C_{10}$, $COOR_3$, where $R_3$ is linear, branched, or cyclic alkyl $C_1-C_{10}$;

Y is selected from the group consisting of phenyl, substituted phenyl where substituents are selected from the group consisting of linear, branched, or cyclic alkyl $C_1-C_{10}$, halogen, $OR_6$ where $R_6$ is linear, branched, or cyclic alkyl $C_1-C_{10}$, aryl, substituted aryl where substituents are selected from the group consisting of linear, branched, or cyclic alkyl $C_1-C_{10}$, halogen, $OR_6$ where $R_6$ is linear, branched, or cyclic alkyl $C_1-C_{10}$, linear, branched, or cyclic alkyl $C_3-C_{10}$;

$R_1$ is selected from the group consisting of phenyl, substituted phenyl where substituents are selected from the group consisting of linear, branched, or cyclic alkyl $C_1$–$C_{10}$, halogen $OR_6$ where $R_6$ is linear, branched, or cyclic alkyl $C_1$–$C_{10}$, aryl, substituted aryl where substituents are selected from the group consisting of linear, branched, or cyclic alkyl $C_1$–$C_{10}$, halogen, $OR_6$ where $R_6$ is linear, branched, or cyclic alkyl $C_1$–$C_{10}$, linear, branched, or cyclic alkyl $C_1$–$C_{10}$, $OR_5$, where $R_5$ is linear, branched, or cyclic alkyl $C_1$–$C_{10}$.

3. The chiral catalyst of claim 1, wherein the aromatic pentatomic biheterocyclic ring of the system is selected from the group consisting of:

3,3'-bithiophene, and the corresponding benzocondensates (II A), (II B), (V A), (V B) and 3,3'-bibenzothiophenes.

4. The chiral catalyst of claim 2, wherein the aromatic pentatomic biheterocyclic ring of the system is 4,4'-biisothiazole.

* * * * *